(12) United States Patent
Ito et al.

(10) Patent No.: US 6,390,816 B2
(45) Date of Patent: May 21, 2002

(54) DENTAL HANDPIECE FOR INJECTING THERAPEUTIC AGENT CONTAINING POWDERS

(75) Inventors: Yukio Ito; Eiichi Nakanishi, both of Kanuma (JP)

(73) Assignee: Nakanishi Inc., Tochigi-Ken (JP)

( * ) Notice: Subject to any disclaimer, the term of this patent is extended or adjusted under 35 U.S.C. 154(b) by 0 days.

(21) Appl. No.: 09/829,970

(22) Filed: Apr. 11, 2001

(30) Foreign Application Priority Data

Apr. 13, 2000 (JP) ........................................ 2000-111735
Apr. 13, 2000 (JP) ........................................ 2000-111739

(51) Int. Cl.[7] ............................................... A61C 3/02
(52) U.S. Cl. ........................................ 433/88; 451/102
(58) Field of Search ................ 433/80, 88; 451/102, 451/60, 38, 99; 604/58, 140, 147

(56) References Cited

U.S. PATENT DOCUMENTS

| | | | |
|---|---|---|---|
| 3,164,153 A | * | 1/1965 | Zorzi ........................... 433/88 |
| 4,522,597 A | * | 6/1985 | Gallant ......................... 433/88 |
| 4,540,365 A | * | 9/1985 | Nelson et al. ................. 433/88 |
| 4,696,645 A | * | 9/1987 | Saupe et al. .................. 433/88 |
| 5,759,031 A | * | 6/1998 | Goldsmith et al. ........... 433/88 |
| 5,857,851 A | * | 1/1999 | Chavanne ..................... 433/88 |
| 6,309,217 B1 | * | 10/2001 | Aumuller ..................... 433/88 |

OTHER PUBLICATIONS

Patent Abs. of JP, 10–286268.
Patent Abs. of JP, 10–179617.

* cited by examiner

Primary Examiner—Cary E. O'Connor
(74) Attorney, Agent, or Firm—Keil & Weinkauf

(57) ABSTRACT

A dental handpiece is disclosed for injecting an air-powder mixture and water against teeth for dental treatment. The handpiece includes a container for accommodating powders, an air supply line for supplying air into the container to produce an air-powder mixture in the container, a mixture transfer line for transferring the mixture, a water supply line for transferring water, and an injection nozzle for injecting the mixture and the water against a treatment site. The container has a curved inner surface for allowing whirl of air spatially in all directions in the container. The air supply line has a plurality of branched lines each extending in the central part of the container to close proximity to the curved inner surface of the container. Each of the branched lines has in its distal part a plurality of ports oriented to direct air flow therethrough along the curved inner surface of the container.

7 Claims, 6 Drawing Sheets

DENTAL HANDPIECE FOR INJECTING THERAPEUTIC AGENT CONTAINING POWDERS

FIELD OF THE INVENTION

The present invention relates to a dental handpiece for injecting an air-powder mixture together with water against teeth for dental treatment.

BACKGROUND OF THE INVENTION

Dental handpieces are known which mix air and powders and inject the resulting mixture against tooth surface together with water for polishing or cleaning teeth.

For example, JP-10-179617-A discloses a dental tool of a handpiece type for injecting therapeutic agent. JP-10-286268-A discloses a dental handpiece for use in prophylaxis treatment of carious teeth by spraying powders mixed with air and water. This handpiece includes a powder container, an air flow line for supplying air into the container, a mixture transfer line for transferring a mixture of powders and air to a spray nozzle, a water supply line for transferring water to the spray nozzle for injection with the mixture against teeth, and tubes each connected to the air flow line or the mixture transfer line and projecting inside the container. The tips of the projecting tubes are perforated to form air outlet ports and mixture inlet ports, respectively.

In dental handpieces of this type, powders must be mixed with air at an appropriate concentration. For this purpose, the projecting tubes are arranged so that the air outlet ports and the mixture inlet ports are positioned substantially in the central region of the container.

This handpiece, however, is likely to be held in various positions during dental treatment by a dentist, so that the concentration of the air-powder mixture in the container may not always be at an appropriate concentration.

Further, when the air supply into the container is stopped with the air outlet ports being immersed in the powders, the powders flow back into the air flow line through the air outlet ports, to thereby cause clogging of the air flow line or decrease in the air supply.

On the other hand, the handpiece is connected to a hose for air and water supply into the air flow line and the water supply line. When the handpiece is moved in various positions during the treatment, the hose is often twisted or entangled to impair operability of the handpiece.

SUMMARY OF THE INVENTION

It is therefore an object of the present invention to provide a dental handpiece that provides improved mixing of powders and air in the container to give a mixture of an appropriate concentration.

It is another object of the present invention to provide a dental handpiece wherein the powder back flow into the air supply line is prevented irrespective of the position of the handpiece.

It is yet another object of the present invention to provide a dental handpiece which prevents twisting or entangling of the hose connected to the handpiece for air and water supply, during the operation of the handpiece.

It is still another object of the present invention to provide a dental handpiece having a nozzle that is hard to be clogged, and that enables concentrated injection of powders onto a particular location such as a gap between teeth.

According to the present invention, there is provided a dental handpiece for injecting an air-powder mixture and water against teeth for dental treatment, comprising:

a container for accommodating powders;

an air supply line for supplying air into said container to produce a mixture of said powders and said air in the container;

a mixture transfer line for transferring said mixture;

a water supply line for transferring water; and an injection nozzle for injecting the mixture received from said mixture transfer line and the water received from said water supply line against a treatment site;

wherein said container has a curved inner surface for allowing whirl of air spatially in all directions in the container, wherein said air supply line has a plurality of branched lines each extending in central part of the container to close proximity to the curved inner surface of the container, each of said branched lines having in its distal part a plurality of ports oriented to direct air flow therethrough along the curved inner surface of the container.

The dental handpiece of the present invention has a plurality of branched air supply lines in the container. Each branched line extends in the central part of the container to close proximity to the curved inner surface, and has in its distal part a plurality of ports oriented to direct the air flow along the curved inner surface of the container. With such structures, the air blown into the container effectively mixes with the powders to produce a mixture of a uniform concentration in the container. The mixture is then transferred through the mixture transfer line and injected through the nozzle against teeth to achieve ideal treatment effect.

The dental handpiece of the present invention may be provided with a check valve in the distal part of each branched line for preventing back flow of the powders into the branched lines through the ports. With such a check valve, back flow of the powders into the air supply line is advantageously prevented irrespective of the position or orientation of the handpiece.

The handpiece of the present invention may also be provided with a grip section between the container and the injection nozzle for an operator to grip. The grip section is preferably connected to the container rotatably and detachably. With such structure, a hose connected to the handpiece for supplying air and water to the air and water supply lines will not be twisted or entangled even when the handpiece is held in various positions during the treatment.

The injection nozzle of the present handpiece may be mounted rotatably with respect to the water supply line and the mixture transfer line. By rotatably disposing the injection nozzle, the operability of the handpiece is improved, and the directions of the mixture and the water injected through the nozzle may be adjusted easily for achieving the optimum treatment effect.

The injection nozzle of the present handpiece may be provided with a mixture transfer line having a mixture injection outlet, and a water transfer line having a water injection outlet, so that the air-powder mixture and the water are transferred and injected separately through the injection nozzle. By providing separate transferring lines and injection outlets for the mixture and the water, clogging of the injection nozzle is advantageously prevented.

The mixture injection outlet may be formed so as to inject the air-powder mixture in a flat stream, and more specifically, the outlet may be formed in the form of a slot. With such an injection outlet generating a flat stream of the mixture, the mixture may be injected easily against every hole and corner of the teeth including gaps between teeth.

The water injection outlet may be arranged to surround the mixture injection outlet. This arrangement further enhances mixing of the water with the air-powder mixture without causing clogging in the injection nozzle.

DETAILED DESCRIPTION OF THE PREFERRED EMBODIMENTS

Preferred embodiments of the present invention will now be explained in detail with reference to the attached drawings, which should be interpreted as merely examples and should not be interpreted in a limiting sense.

Figure 1:
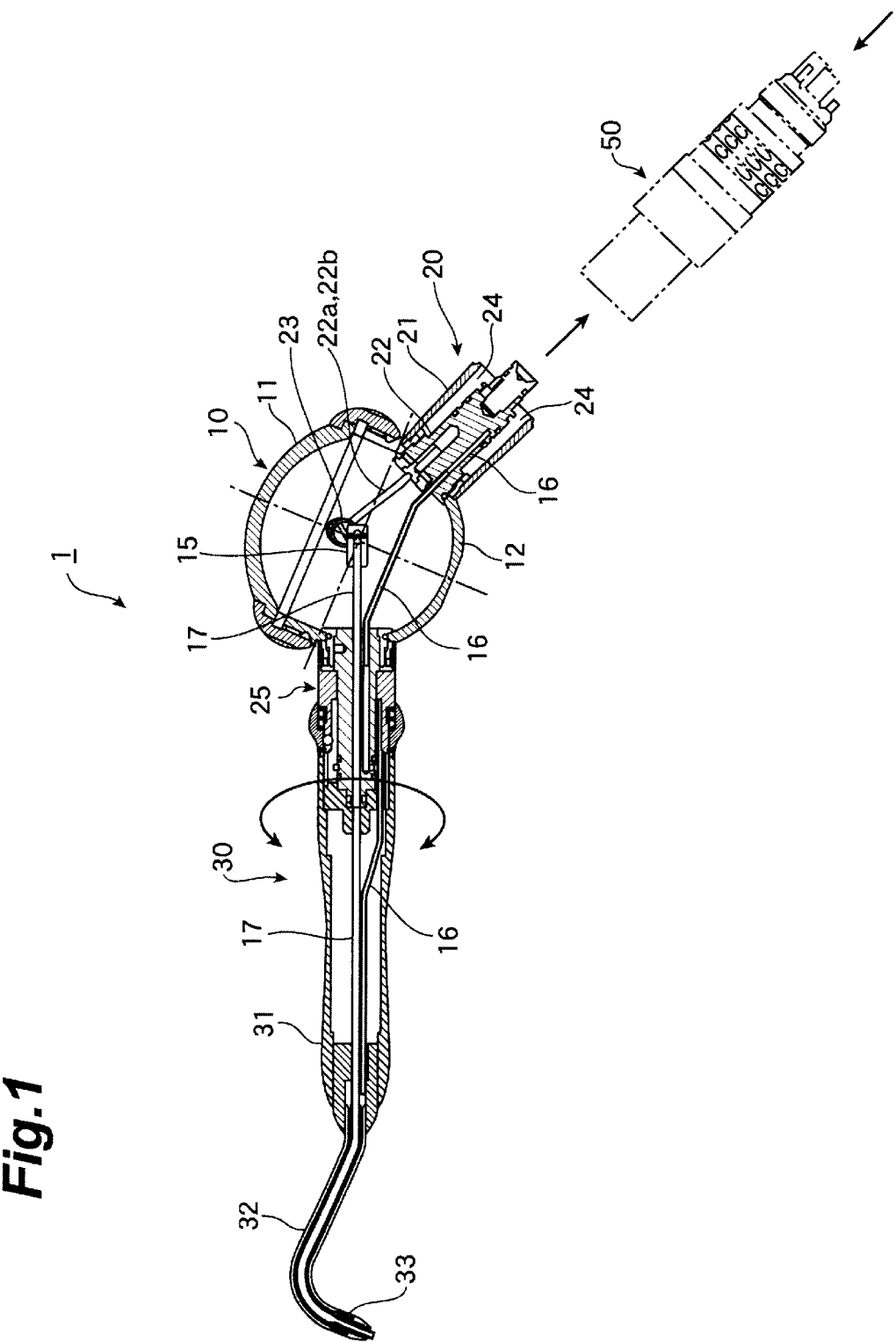
FIG. 1 is a longitudinal sectional view of a dental handpiece according to the present invention.

FIG. 1 is a longitudinal sectional view of an embodiment of the dental handpiece according to the present invention. Dental handpiece 1 has powder container 10 for accommodating powders therein, nozzle unit 20 connected to the powder container 10, connecting section 25 connected to the container 10 on the opposite side from the nozzle unit 20, and grip section 30 connected to the connecting section 25 and having on its distal end injection nozzle 33.

Figure 2:
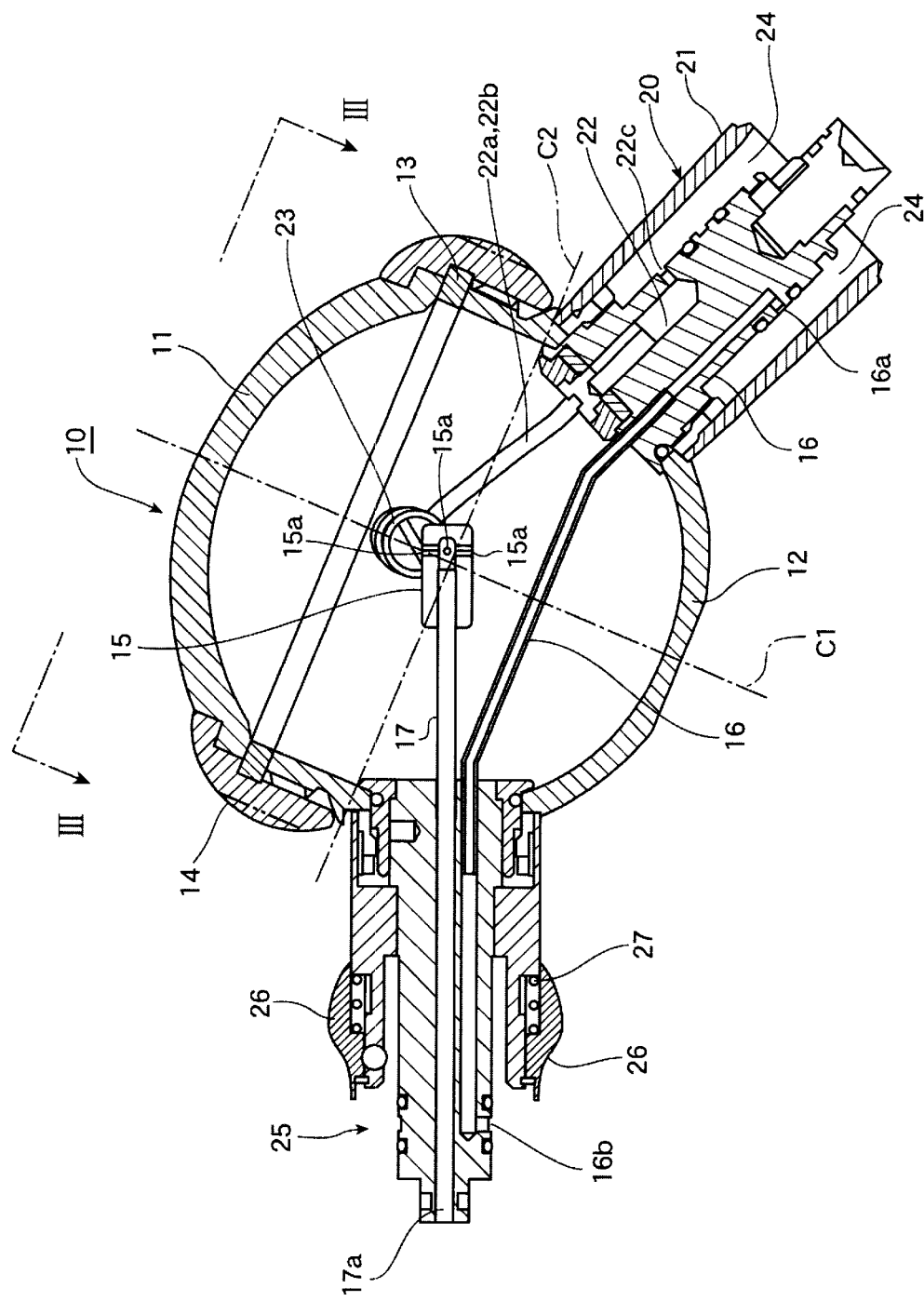
FIG. 2 is an enlarged sectional view of FIG. 1 showing the details around the powder container.

Referring to FIG. 2, showing the details around the powder container 10, the powder container 10 includes upper curved body 11 and lower curved body 12, which are connected sealably with securing ring 14 via packing 13. The upper curved body 11 may open and close the lower curved body 12. Each of the upper and lower curved bodies 11 and 12 is formed of a hollow curved body that constitutes a part of a hollow sphere having a different diameter. The inner surface of the upper and lower curved bodies 11 and 12 are curved so as to allow the air sprayed into the container to efficiently whirl to thereby achieve enhanced mixing with the powders in the container. To the lower curved body 12, the nozzle unit 20 and the connecting section 25 are connected on opposite sides of the container 10 at an angle to each other.

Figure 3:
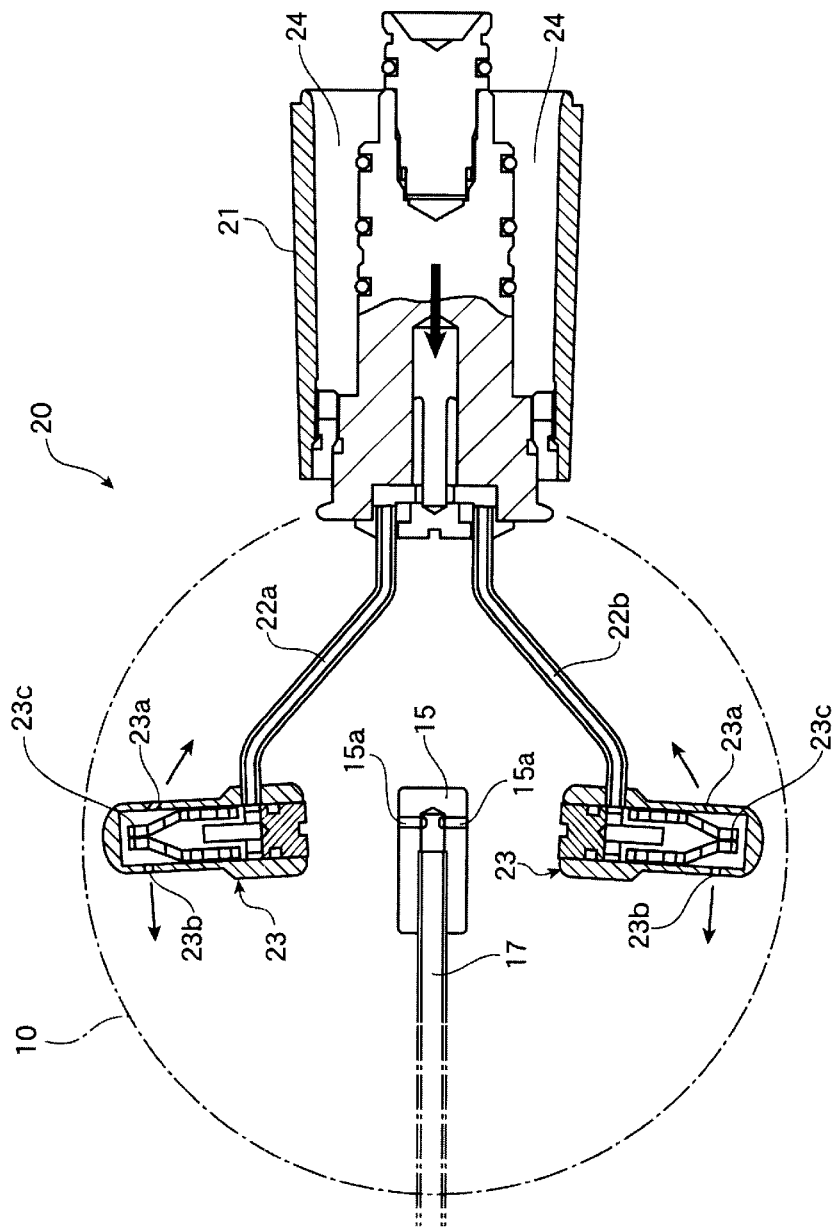
FIG. 3 is an enlarged sectional view taken along lines III—III in FIG. 2, illustrating the air spray nozzles.

The nozzle unit 20 includes, as shown in detail in FIG. 3, connector portion 21 for fixedly connecting to the lower curved body 12, water supply line 16 (FIG. 1) extending through the connector portion 21 for transferring water, air supply line 22 extending through the connector portion 21 for supplying air into the powder container 10, two branched lines 22a, 22b branched from the air supply line 22, and an air spray nozzle 23 connected to the distal end of each of the branched lines 22a, 22b.

The connector portion 21 has recess 24 for receiving and rotatably holding coupling 50 shown in phantom in FIG. 1. The other end of the coupling 50 is connected to a hose (not shown) for supplying air and water from respective sources (not shown) into the air supply line 22 and the water supply line 16, respectively. The rotatable connection between the connector portion 21 and the coupling 50 prevents the hose from being twisted or entangled even when the handpiece 1 is held in various positions or orientations during the treatment.

The connector portion 21 also has ports 16a and 22c each provided through the inner wall of the recess 24.

The port 16a is in communication with the water supply line 16 for transferring the water from the source through the hose and the coupling 50 into the water supply line 16. The water supply line 16 extends from the port 16a through the connector portion 21, across the container 10, and through the connecting section 25 to port 16b in the connecting section 25 as will be discussed later.

The port 22c is in communication with the air supply line 22 for transferring the air from the source through the hose and the coupling 50 into the air supply line 22. The air supply line 22 extends through the connector portion 21 into the container 10, and is branched into two branched lines 22a, 22b in the container. The branched lines 22a, 22b extend in opposite directions from near the crossing point of dashed lines C1 and C2 in FIG. 2, in other words, in the central region of the container 10, toward the curved inner surface of the container 10.

The air spray nozzle 23 is connected to the distal end of each of the branched lines 22a, 22b, and is arranged in proximity to the inner surface of the container 10. The air spray nozzle 23 has outlet ports 23a, 23b arranged opposite to each other and oriented to direct the air flow therethrough to multiple directions along the inner surfaces of the upper and lower curved bodies 11 and 12. Though not shown in the drawings, it is preferred to provide the air spray nozzle 23 with two more outlet ports in addition to and at locations 90° apart from the ports 23a, 23b in order to further enhance the whirl of the air in the container 10.

The air spray nozzle 23 is also provided therein with a check valve 23c for preventing back flow of the powders in the container 10 through the outlet ports 23a, 23b into the branched lines 22a, 22b.

In approximately the center of the container 10, mixture inlet member 15 is located for taking in the air-powder mixture produced in the container 10. The mixture inlet member 15 has a plurality of inlet ports 15a, which communicate with mixture transfer line 17 for transferring the air-powder mixture. The mixture transfer line 17 is connected to the mixture inlet member 15 and extends distally from approximately the center of the container 10 into the connecting section 25.

The connecting section 25 is fixedly connected to the lower curved body 12 at an angle to the nozzle unit 20 arranged on the opposite side of the container 10. The connecting section 25 encloses the water supply line 16 extending therethrough to the port 16b provided in the distal part of the section 25. The mixture transfer line 17 also extends through the section 25 for transferring the air-powder mixture from inside the container 10 to port 17a provided in the distal part of the section 25.

The connecting section 25 is provided with a connector ring 26 located opposite to the container 10. The connector ring 26 is thrust by spring 27 for detachably and rotatably holding the grip section 30 with respect to the connecting section 25.

The grip section 30 includes casing 31, neck portion 32 extending from the distal end of the casing 31, and injection nozzle 33 provided on the distal end of the neck portion 32.

Figure 4A:
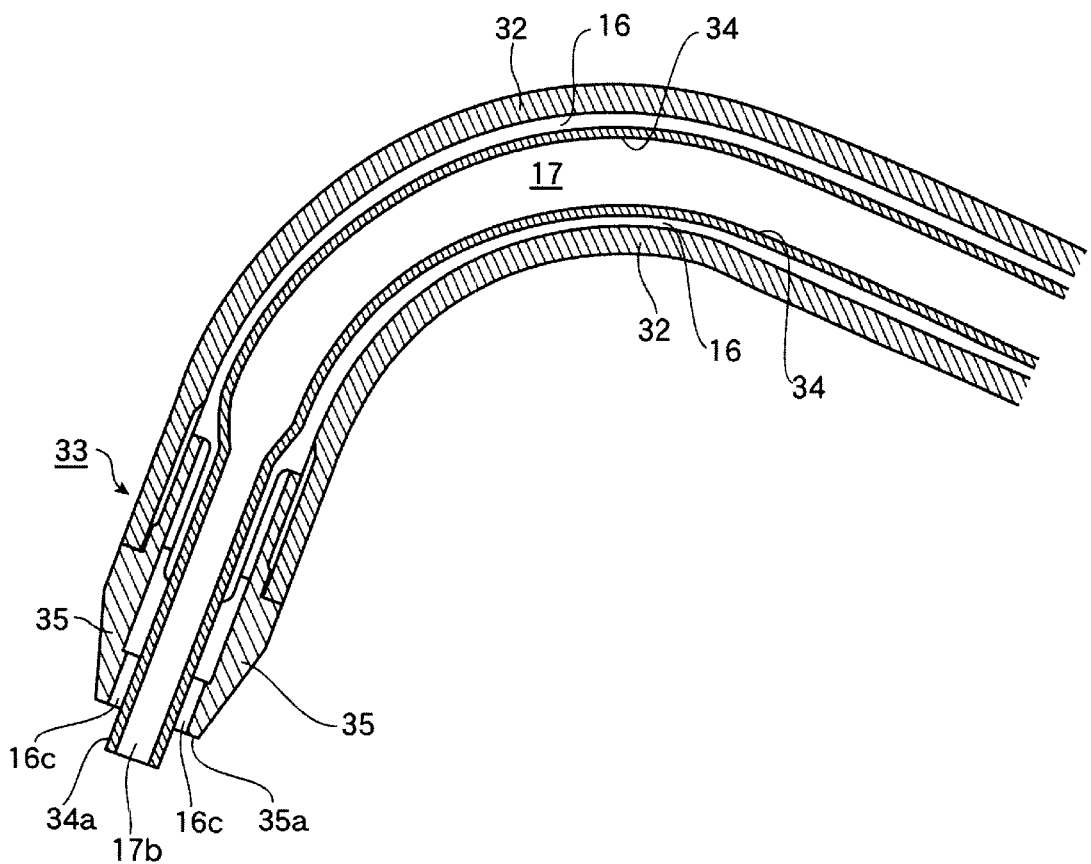
FIG. 4(a) is an enlarged sectional view of the injection nozzle shown in FIG. 1.
Figure 4B:
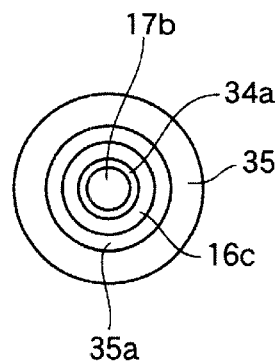
FIG. 4(b) is an end view of the same injection nozzle.

The mixture transfer line 17 extends from the port 17a in the connecting section 25 through the casing 31 and the neck portion 32 to mixture injection outlet 17*b* (FIG. 4(*a*)) in the injection nozzle 33. The water supply line 16 extends from the port 16*b* in the connecting section 25 through the casing 31 and the neck portion 32 to water injection outlet 16*c* in the injection nozzle 33.

As shown in the longitudinal sectional view in FIG. 4(*a*) and the end view in FIG. 4(*b*), the lines 16 and 17 are arranged in a double tube from the distal end portion of the casing 31 through the neck portion to the nozzle 33. The double tube includes outer tube 32 and inner tube 34, with the inner surface of the outer tube 32 and the outer surface of the inner tube 34 forming the water supply line 16, and the inner surface of the inner tube 34 forming the mixture transfer line 17. Tip member 35 is connected to the distal end of the outer tube 32 to narrow the water supply line 16, forming the water injection outlet 16*c*. The distal part of the inner tube 34 is narrowed toward its distal end to form a reduced diameter portion 34*a*. The distal part of the reduced diameter portion 34*a* extends beyond the end face 35*a* of the tip member 35 to form mixture injection outlet 17*b*.

With such structure, the air-powder mixture is injected through the mixture injection outlet 17*b* positioned in the center of the end face of the injection nozzle 33, while the water is injected through the water injection outlet 16*c* arranged surrounding the mixture injection outlet 17*b*, so that the water and the mixture are injected simultaneously against tooth surface.

The operation of the handpiece 1 will now be explained.

When water is supplied to the handpiece 1 via a hose (not shown) and the coupling 50, the water enters through the port 16*a* into the water supply line 16, which extends through the connector portion 21, across the container 10, and through the connecting section 25, and further through the grip section 30, via the port 16*b*. The water is then injected through the injection nozzle 33 via the water injection outlet 16*c*.

On the other hand, the air supplied via the hose and the coupling 50 enters through the port 22*c* into the air supply line 22, and branched into the branched lines 22*a*, 22*b* to reach the air spray nozzles 23. The air is then sprayed through the outlet ports 23*a*, 23*b* of the nozzles 23 in multiple directions along the curved inner surface of the container 10 to produce a substantially homogeneous mixture with the powders in the container 10.

The sprayed air increases the pressure in the container 10, which forces the homogeneous mixture to flow into the mixture inlet member 15 through the inlet ports 15*a* and pass through the mixture transfer line 17 extending through the connecting section 25 and the grip section 30. The mixture then reaches the injection nozzle 33 and injected via the mixture injection outlet 17*b*, surrounded by the water stream through the outlet 16*c*.

As such, the air-powder mixture and the water are guided through different supply lines, and injected simultaneously through the injection nozzle 33 against tooth surface to polish or clean the tooth surface.

Figure 5:
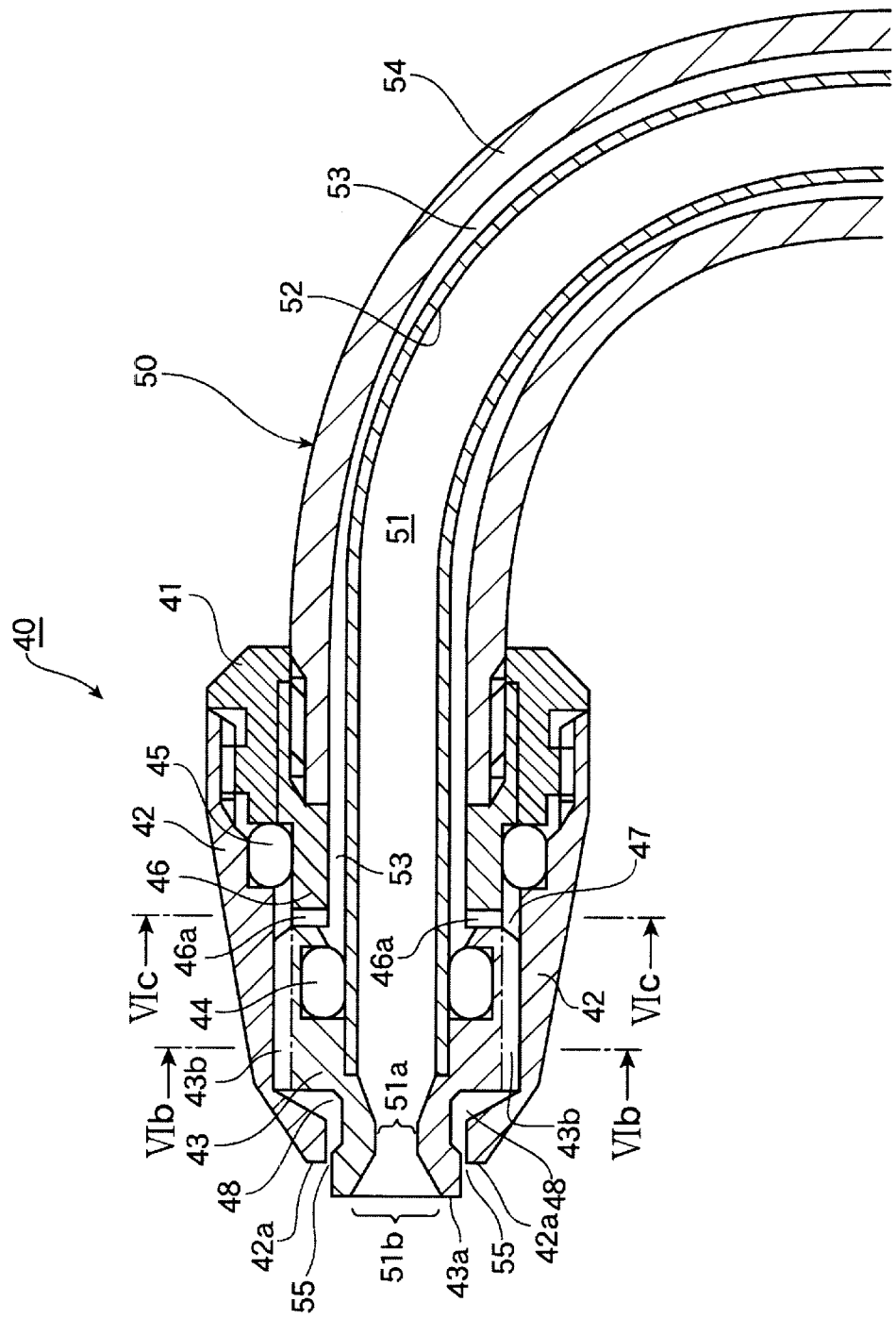
FIG. 5 is an enlarged sectional view of another embodiment of the injection nozzle used in the present invention.
Figure 6A:
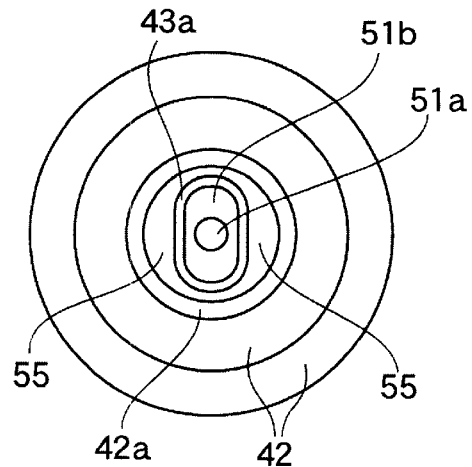
FIG. 6(a) is an end view of the injection nozzle of FIG. 5.
Figure 6B:
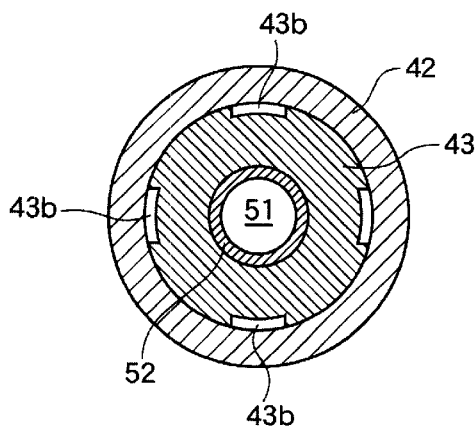
FIG. 6(b) is a sectional view taken along lines VIb—VIb in FIG. 5.
Figure 6C:
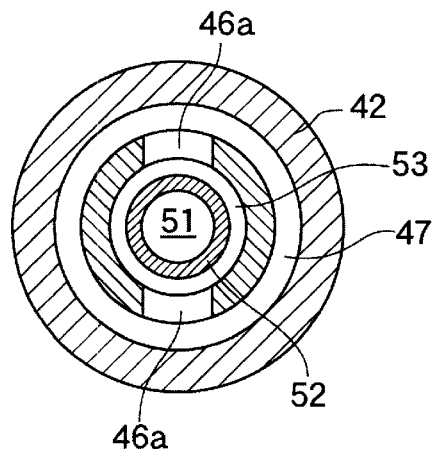
FIG. 6(c) is a a sectional view taken along lines VIc—VIc in FIG. 5.

FIGS. 5 and 6 illustrate another embodiment of an injection nozzle that may be used in the handpiece of the present invention.

Referring to FIG. 5, injection nozzle 40 is rotatably mounted on the distal part of neck portion 50 of a handpiece. The neck portion 50 is formed as a double tube having inner tube 52 and outer tube 54, with the inner surface of the outer tube 54 and the outer surface of the inner tube 52 defining water supply line 53 and the inner surface of the inner tube 52 defining mixture transfer line 51.

The injection nozzle 40 includes an air-powder mixture transfer line having injection outlet 51*b* in communication with the mixture transfer line 51, and a water supply line having injection outlet 55 in communication with the water supply line 53.

More specifically, the injection nozzle 40 includes fixed member 46 fixed on the distal portion of the outer tube 54, rear end member 41 abutting and mounted slidably and rotatably with respect to the fixed member 46, front end member 43 abutting and mounted slidably and rotatably with respect to the distal end of the inner tube 52, and outer sheath 42 rotatably joining the rear end member 41 and the front end member 43 together. The gap between the outer sheath 42 and the fixed member 46 is sealed with o-ring 45, and the gap between the inner tube 52 and the front end member 43 is sealed with o-ring 44, as packings for preventing water leakage.

The fixed member 46 abuts the distal end of the outer tube 54, and defines with the inner tube 52 the water supply line 53. The fixed member 46 is provided with cut-out grooves 46*a* in the distal end portion thereof at vertically opposing positions, as best seen in FIG. 6(*c*). The water passed through the water supply line 53 flows radially outwardly through the cut-out grooves 46*a* and enters annular gap 47 formed between the fixed member 46 and the outer sheath 42.

The front end member 43 has cut-out grooves 43*b* extending axially on the outer periphery thereof, as shown in FIGS. 5 and 6(*b*). The grooves 43*b* define with the inner surface of the outer sheath 42 passages for the water, which passages are in communication with the water supply line 53 via the grooves 46*a* in the fixed member and the gap 47. The outer diameter of the front end member 43 is reduced at a region distal to the grooves 43 to define with the inner surface of the outer sheath 42 an annular gap 48 acting as a passage for the water in communication with the grooves 43*b*. The front end member 43 ends with front end face 43*a* having a flat elliptic contour as shown in FIG. 6(*a*).

The inner surface of the front end member 43 is distally tapered toward reduced diameter portion 51*a*, and then flared from the portion 51*a* toward the front end face 43*a*, defining the distal part of the mixture transfer line 51. The mixture transfer line 51 ends with vertically elongated flat elliptic injection outlet, or slot, 51*b* for injecting the mixture in the form of a flat stream.

The outer sheath 42 is distally tapered, and has distal end face 42*a* of a circular ring shape, surrounding the front end face 43*a* of the front end member 43. The inner surface of the outer sheath 42 defines with the outer surface of the front end member 43 injection outlet 55 for the water in communication with the gap 48. The outlet 55 is vertically elongated and horizontally widened on the right and left sides of the injection outlet 51*b* and vertically narrowed on the top and bottom sides of the injection outlet 51*b*, as best seen in FIG. 6(*a*).

The operation of the nozzle 40 will now be discussed.

The air-powder mixture passes through the mixture transfer line 51 to reach the reduced diameter portion 51*a*, flows along the flared surface, and injected through the injection outlet 51*b* in the form of a flat stream.

On the other hand, the water flows through the water supply line 53, passes through the grooves 46*a* to enter the gap 47, and then flows through the grooves 43*b* and the gap 48, and injected through the injection outlet 55 in the form of an annular flat stream.

The mixture injected through the injection outlet 51*b* and the water injected through the injection outlet 55 are mixed while they are in the air in the form of flat streams, or upon their impingement on tooth surface. Thus the mixture and the water are concentrically injected against a particular portion such as a gap between teeth for effective dental treatment.

Further, the nozzle 40 may be rotated around the longitudinal axis in order to change the direction of the injection outlets 51b and 55 in conformity with the shape of the treatment site for further improvement in the concentrated injection.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece for injecting an air-powder mixture and water against teeth for dental treatment, comprising:
   a container for accommodating powders;
   an air supply line for supplying air into said container to produce a mixture of said powders and said air in the container;
   a mixture transfer line for transferring said mixture;
   a water supply line for transferring water; and
   an injection nozzle for injecting the mixture received from said mixture transfer line and the water received from said water supply line against a treatment site;
   wherein said container has a curved inner surface for allowing whirl of air spatially in all directions in the container,
   wherein said air supply line has a plurality of branched lines each extending in central part of the container to close proximity to the curved inner surface of the container, each of said branched lines having in its distal part a plurality of ports oriented to direct air flow therethrough along the curved inner surface of the container.

2. The dental handpiece of claim 1 further comprising a check valve provided in a distal part of each of said branched lines for preventing back flow of the powders into the branched lines through the ports.

3. The dental handpiece of claim 1 further comprising a grip section between said container and said injection nozzle for gripping by an operator, wherein said grip section is connected rotatably and detachably to the container.

4. The dental handpiece of claim 1, wherein said injection nozzle is rotatably mounted with respect to said water supply line and said mixture transfer line.

5. The dental handpiece of claim 1, wherein said injection nozzle has a mixture transfer line having a mixture injection outlet, and a water transfer line having a water injection outlet, and the mixture and the water are transferred and injected separately through the injection nozzle.

6. The dental handpiece of claim 5, wherein said mixture injection outlet in said injection nozzle is in a shape for injecting the mixture in a flat stream.

7. The dental handpiece of claim 5, wherein said water injection outlet surrounds said mixture injection outlet.

* * * * *